(12) United States Patent
Kelfkens et al.

(10) Patent No.: US 9,416,077 B2
(45) Date of Patent: Aug. 16, 2016

(54) RENEWABLE CARBON CONTENT IN METHANOL AND OTHER PRODUCTS FROM GASIFICATION OF BIOMASS

(71) Applicant: Sundrop Fuels, Inc., Longmont, CO (US)

(72) Inventors: Renus Constantyn Kelfkens, Longmont, CO (US); Herbert Mark Kosstrin, Wellesley, MA (US)

(73) Assignee: Sundrop Fuels, Inc., Longmont, CO (US)

( * ) Notice: Subject to any disclaimer, the term of this patent is extended or adjusted under 35 U.S.C. 154(b) by 116 days.

(21) Appl. No.: 14/026,768

(22) Filed: Sep. 13, 2013

(65) Prior Publication Data

US 2014/0080928 A1    Mar. 20, 2014

Related U.S. Application Data

(60) Provisional application No. 61/701,303, filed on Sep. 14, 2012.

(51) Int. Cl.
| | | |
|---|---|---|
| C07C 29/15 | (2006.01) | |
| C07C 29/151 | (2006.01) | |
| C07C 31/00 | (2006.01) | |

(Continued)

(52) U.S. Cl.
CPC ............. C07C 29/1518 (2013.01); *Y02E 50/18* (2013.01)

(58) Field of Classification Search
CPC ........ B01J 19/00; C07C 29/15; C07C 29/151; C07C 29/1516; C07C 29/1518; C07C 31/00–31/04; Y02E 50/10; Y02E 50/18; C10J 2300/00; C10J 2300/09; C10J 2300/0913–2300/092; C10J 2300/18–2300/1823; C10J 2300/1853
See application file for complete search history.

(56) References Cited

U.S. PATENT DOCUMENTS 5,496,859 A * 3/1996 Fong .......................... C01B 3/36
                                                        252/373
6,645,442 B2    11/2003 Keneko et al.

(Continued)

OTHER PUBLICATIONS

Higuchi, Takayoshi "Steam Explosion of Wood", Sections 1-4, Biomass Handbook, © 1989 by OPA (Amsterdam), pp. 470-473 plus Cover, Biblio, Table of Contents excerpt. 7 pages total, Editors: Osamu Kitani & Carl W. Hall, ISBN 2-88124-269-3, Gordon and Breach Science Publishers S. A., Cooper Station, New York, New York.

(Continued)

*Primary Examiner* — Natasha Young
(74) *Attorney, Agent, or Firm* — Rutan & Tucker, LLP (57) ABSTRACT

An integrated plant is provided to improve carbon utilization of carbon molecules from gasified woody biomass to be converted into methanol. Detectors ensure a minimized sulfur content of less than 0.05% by dry weight of the woody biomass. A biomass gasifier reacts woody biomass in a rapid gasification reaction to produce a syngas composition having a ratio of hydrogen to carbon dioxide that is higher than needed for methanol synthesis. Parallel to the gasifier, a hydrocarbon reforming reactor provides a syngas composition having a ratio of hydrogen to carbon monoxide that is higher than needed for methanol synthesis. The combined syngas mixture from the biomass gasifier and the hydrocarbon reforming reactor comprises feed to a methanol synthesis plant, such that a majority of the carbon dioxide produced by the biomass gasification reaction and the hydrogen produced by the hydrocarbon reforming reactor are synthesized into methanol.

15 Claims, 5 Drawing Sheets

(51) Int. Cl.
*C07C 31/02* (2006.01)
*C07C 31/04* (2006.01)
*B01J 19/00* (2006.01)

(56) References Cited

U.S. PATENT DOCUMENTS

| | | | |
|---|---|---|---|
| 6,767,375 B1 * | 7/2004 | Pearson | C10J 3/485 |
| | | | 48/111 |
| 6,872,378 B2 | 3/2005 | Weimer et al. | |
| 6,991,769 B2 | 1/2006 | Kaneko et al. | |
| 7,033,570 B2 | 4/2006 | Weimer et al. | |
| 7,294,225 B2 | 11/2007 | Landaiv et al. | |
| 7,553,476 B2 | 6/2009 | Marrella et al. | |
| 7,632,476 B2 | 12/2009 | Shah et al. | |
| 7,686,856 B2 | 3/2010 | Hemmings et al. | |
| 7,856,829 B2 | 12/2010 | Shah et al. | |
| 7,871,457 B2 | 1/2011 | Shah et al. | |
| 7,881,825 B2 | 2/2011 | Esposito et al. | |
| 7,931,888 B2 | 4/2011 | Drnevich et al. | |
| 7,985,399 B2 | 7/2011 | Drnevich et al. | |
| 8,007,761 B2 | 8/2011 | Drnevich et al. | |
| 8,709,112 B2 | 4/2014 | Hilton et al. | |
| 8,771,387 B2 | 7/2014 | Simmons et al. | |
| 8,821,599 B2 | 9/2014 | Perkins et al. | |
| 9,011,560 B2 | 4/2015 | Simmons et al. | |
| 2002/0159929 A1 * | 10/2002 | Kaneko et al. | 422/190 |
| 2003/0182861 A1 | 10/2003 | Weimer et al. | |
| 2003/0208959 A1 | 11/2003 | Weimer et al. | |
| 2005/0032920 A1 | 2/2005 | Norbeck et al. | |
| 2006/0140848 A1 | 6/2006 | Weimer et al. | |
| 2006/0188433 A1 | 8/2006 | Weimer et al. | |
| 2007/0129450 A1 * | 6/2007 | Barnicki | C10G 2/30 |
| | | | 518/704 |
| 2008/0161428 A1 * | 7/2008 | Strait | C01B 3/586 |
| | | | 518/702 |
| 2009/0013601 A1 | 1/2009 | Mandich et al. | |
| 2009/0313886 A1 | 12/2009 | Hinman | |
| 2009/0324458 A1 * | 12/2009 | Robinson | C10J 3/00 |
| | | | 422/187 |
| 2010/0000874 A1 | 1/2010 | Hinman | |
| 2010/0137459 A1 | 6/2010 | Stites et al. | |
| 2010/0157730 A1 | 6/2010 | Bradford | |
| 2010/0186291 A1 | 7/2010 | Yie et al. | |
| 2010/0243961 A1 | 9/2010 | Hilton | |
| 2010/0249251 A1 | 9/2010 | Hilton | |
| 2010/0270505 A1 | 10/2010 | Gallaspy et al. | |
| 2010/0273899 A1 | 10/2010 | Winter | |
| 2011/0107661 A1 | 5/2011 | Tirmizi et al. | |
| 2011/0124927 A1 | 5/2011 | Stites et al. | |
| 2011/0155958 A1 | 6/2011 | Winter et al. | |
| 2012/0145965 A1 | 6/2012 | Simmons et al. | |
| 2012/0156742 A1 | 6/2012 | Powell et al. | |
| 2012/0157730 A1 | 6/2012 | Powell et al. | |
| 2012/0174471 A1 | 7/2012 | Powell et al. | |
| 2012/0181483 A1 | 7/2012 | Simmons et al. | |

OTHER PUBLICATIONS

"StakeTech—First Pulping System Receives Full Acceptance", May 14, 1996, 2 pages. Publisher: Business Wire. downloaded from http://www.thefreelibrary.com/StakeTech.

McCallum, Don, "Medium Density Fiber Board" pp. 8-11, Nov. 1, 1996 http://fennerschool-associated.anu.edu.au/fpt/mdf/manufacture.html.

Notification of Transmittal of the International Search Report and the Written Opinion for PCT/US13/59782 mailed Jan. 29, 2014, 8 pages. International Searching Authority/US, Alexandria, Virginia, USA.

* cited by examiner

| Example | Model | D10 (μm) | D50 (μm) | D90 (μm) | Avg. Aspect |
|---|---|---|---|---|---|
| SEP White Pine #1 | xc-min | 20.4 | 59.8 | 176 | 0.47 |
| SEP White Pine #2 | xc-min | 23.9 | 71.7 | 213 | 0.48 |
| SEP White Pine #2 - a | xc-min | 21.7 | 65.3 | 197 | 0.49 |
| SEP White Pine #3 | xc-min | 23 | 59.5 | 182 | 0.47 |
| SEP Mixed Hardwood #4 | xc-min | 39.3 | 175.0 | 404.1 | - |
| SEP Black Spruce #5 | xc-min | 25.6 | 94.4 | 320 | 0.45 |
| SEP White Pine #1 | Fe-max | 34.5 | 158 | 541 | 0.47 |
| SEP White Pine #2 | Fe-max | 41.4 | 186 | 660 | 0.45 |
| SEP White Pine #2 – a | Fe-max | 39.2 | 176 | 584 | 0.46 |
| SEP White Pine #3 | Fe-max | 42.9 | 186 | 629 | 0.45 |

*Figure 5*

RENEWABLE CARBON CONTENT IN METHANOL AND OTHER PRODUCTS FROM GASIFICATION OF BIOMASS

RELATED APPLICATIONS

This application claims the benefit of and priority to U.S. Provisional application, entitled "Improving Renewable Carbon Content in Methanol and Other Products from Gasification of Biomass," filed on Sep. 14, 2012 having application Ser. No. 61/701,303.

FIELD

The design generally relates to treatment of low sulfur content raw gas from a biomass gasifier in pre-process methods where acid gas need not be removed and in an embodiment specifically to an integrated plant that uses this biomass to produce a liquid fuel from the biomass or to convert the biomass into a densified form to facilitate economic transport to facilities for further processing to liquid fuel, heat/power, animal feed, bedding, or chemicals.

BACKGROUND

A conventional configuration of a biomass decomposition and methanol synthesis process leads to a great deal of valuable biomass carbon being lost as CO2. This result is a lower methanol product yield and a higher carbon footprint. What is needed, therefore, is an integrated plant that improves carbon utilization of carbon molecules from gasified biomass such that a majority of the carbon dioxide and the hydrogen produced are synthesized into methanol.

SUMMARY

The design provides a method and apparatus for an integrated plant to improve carbon utilization of carbon molecules from gasified woody biomass to be converted into methanol. Detectors ensure a minimized sulfur content of less than 0.05% by volume of the woody biomass. A biomass gasifier reacts woody biomass in a rapid gasification reaction to produce a syngas composition having a ratio of hydrogen to carbon dioxide that is higher than needed for methanol synthesis. Parallel to the gasifier, a hydrocarbon reforming reactor provides a syngas composition having a ratio of hydrogen to carbon monoxide that is higher than needed for methanol synthesis. The combined syngas mixture from the biomass gasifier and the hydrocarbon reforming reactor comprises feed to a methanol synthesis plant, such that a majority of the carbon dioxide produced by the biomass gasification reaction and the hydrogen produced by the hydrocarbon reforming reactor are synthesized into methanol.

The biomass gasifier comprises a radiant high heat-flux reactor configured to react the woody biomass received from a biomass feed system in moist fine particle form at a temperature of at least 950 degrees C. A steam explosion unit configures the woody biomass into the moist fine particle form, characterized by a decreased particle size and an overall increase in surface area. The biomass gasifier has a steam supply input and one or more heat sources. While in the presence of the steam, the woody biomass is reacted in a rapid biomass gasification reaction to produce syngas components comprising hydrogen ($H_2$), carbon dioxide ($CO_2$), and carbon monoxide ($CO$).

Cooperating with and operating in parallel with the biomass gasifier is a hydrocarbon reforming reactor configured to produce a hydrogen-rich syngas composition, having a ratio of hydrogen to carbon monoxide that is higher than generally needed for methanol synthesis. The biomass gasifier produces a potentially carbon dioxide rich syngas composition having a ratio of hydrogen to carbon dioxide that is higher than generally needed for methanol synthesis. The cooperation of the hydrocarbon reforming reactor and the biomass gasifier produces a high quality combined syngas mixture for methanol synthesis, in which greater than 60% of the carbon-based molecules in the woody biomass are converted into methanol in a downstream methanol synthesis plant.

Detectors are geographically located on the same site as the integrated plant. The detectors are configured to measure a sulfur content of the woody biomass so as to ensure a minimized sulfur content of the woody biomass. Minimizing the sulfur content of the woody biomass enables the integrated plant to operate without a water-gas-shift unit and without an acid gas removal unit. The detectors may operate in conjunction with a stored database which maintains a listing of varieties of low-sulfur containing trees that are suitable for creating woody biomass, such that the woody biomass feed produced from each variety of tree possesses a minimized sulfur content of less than 0.05% by dry weight of the woody biomass. In one embodiment, the detectors are configured to ensure that the woody biomass to be feed for the biomass gasifier possesses a minimized sulfur content of less than 0.01% by dry weight of the woody biomass.

Downstream of the biomass gasifier and the hydrocarbon reforming reactor, and upstream of the methanol synthesis plant are sulfur guard fixed beds configured to remove gas contaminants from the combined syngas mixture. The combined syngas mixture from the biomass gasifier and the hydrocarbon reforming reactor comprises feed to the methanol synthesis plant, such that a majority of the carbon dioxide produced by the biomass gasification reaction and the hydrogen produced by the hydrocarbon reforming reactor are synthesized into methanol.

BRIEF DESCRIPTION OF THE DRAWINGS

The drawings refer to embodiments of the design in which.

While the design is subject to various modifications and alternative forms, specific embodiments thereof have been shown by way of example in the drawings and will herein be described in detail. The design should be understood to not be limited to the particular forms disclosed, but on the contrary, the intention is to cover all modifications, equivalents, and alternatives falling within the spirit and scope of the design.

DETAILED DISCUSSION

In the following figures and description, numerous specific details are set forth, such as examples of specific chemicals, named components, connections, types of heat sources, etc., in order to provide a thorough understanding of the present invention. It will be apparent, however, to one skilled in the art that the present invention may be practiced without these specific details. In other instances, well known components or methods have not been described in detail but rather in a block diagram in order to avoid unnecessarily obscuring the design. Thus, the specific details set forth are merely exemplary. The specific details may be varied from and still be contemplated to be within the spirit and scope of the present invention.

While the design is subject to various modifications and alternative forms, specific embodiments thereof have been shown by way of example in the drawings and will herein be described in detail. The design should be understood to not be limited to the particular forms disclosed, but on the contrary, the intention is to cover all modifications, equivalents, and alternatives falling within the spirit and scope of the design.

In general, a method and apparatus are provided for an integrated plant to improve carbon utilization of carbon molecules from gasified woody biomass to be converted into methanol. A biomass gasifier comprising a radiant high heat-flux reactor is configured to react woody biomass received from a biomass feed system in moist fine particle form at a temperature of at least 950 degrees C. The moist fine particle form of the woody biomass is characterized by a decreased particle size and an overall increase in surface area due to being processed in a steam explosion unit. The steam explosion unit and the biomass gasifier are part of the integrated plant. The biomass gasifier has a steam supply input and one or more heat sources. While in the presence of the steam, the woody biomass in moist fine particle form is reacted in the radiant high heat-flux reactor in a rapid biomass gasification reaction to produce at least syngas components comprising hydrogen ($H_2$) carbon dioxide ($CO_2$), and carbon monoxide ($CO$). In one embodiment, the biomass gasifier is configured to react the woody biomass received from the biomass feed system in an oxidation free environment to produce syngas components such that the carbon dioxide ($CO_2$) comprises less than 50% by volume of the syngas.

Operating in parallel with and cooperating with the radiant high heat-flux reactor is a hydrocarbon reforming reactor configured to receive a methane-based gas. The hydrocarbon reforming reactor provides 1) hydrogen gas, 2) a hydrogen-rich syngas composition, in which a ratio of hydrogen ($H_2$) to carbon monoxide ($CO$) is higher than a ratio generally needed for methanol synthesis, and 3) any combination of the two. The biomass gasifier produces a potentially carbon dioxide ($CO_2$) rich syngas composition in which a ratio of hydrogen to carbon dioxide ($H_2:CO_2$) is higher than the ratio generally needed for methanol synthesis. The cooperation of the hydrocarbon reforming reactor and the biomass gasifier produces a high quality combined syngas mixture for methanol synthesis, in which greater than 60% of the carbon-based molecules in the woody biomass received from the biomass feed system are converted into methanol by way of a methanol synthesis plant.

In one embodiment, the hydrocarbon reforming reactor is configured to supply a volume of hydrogen ($H_2$) to the combined syngas mixture such that a ratio of the hydrogen to the sum of the carbon monoxide and the carbon dioxide ($H_2:(CO+CO_2)$) of the combined syngas mixture is between 2.1 and 2.8. In another embodiment, the hydrocarbon reforming reactor is configured to supply a quantity of hydrogen ($H_2$) to the combined syngas mixture such that an exit flue gas from the methanol synthesize plant contains less than 3% of a total quantity of carbon-based molecules fed into the biomass gasifier. In still another embodiment, the hydrocarbon reforming reactor is configured to supply the quantity of hydrogen ($H_2$) to the combined syngas mixture such that less than 9% of the total quantity of carbon-based molecules fed into the biomass gasifier are not converted into gasoline (i.e. >91% conversion).

Detectors are geographically located on the same site as the radiant high heat-flux reactor. The detectors are configured to measure a sulfur content of the woody biomass and are configured to ensure a minimized sulfur content of the woody biomass such that the integrated plant may operate without a water-gas-shift unit and without an acid gas removal unit. In one embodiment, the detectors are configured to work in conjunction with a stored database which maintains a listing of varieties of trees that are suitable for creating woody biomass. The stored database may list a sulfur content and geographical location for each variety of tree, such that the woody biomass feed produced from each variety of tree possesses a minimized sulfur content of less than 0.05% by dry weight of the woody biomass. In another embodiment, the detectors are configured to ensure that the woody biomass to be feed for the biomass gasifier possesses a minimized sulfur content of less than 0.01% by dry weight of the woody biomass.

Downstream of the biomass gasifier and the hydrocarbon reforming reactor, and upstream of the methanol synthesis plant is a sulfur removal unit which is configured to remove gas contaminants from the combined syngas mixture. The combined syngas mixture from the biomass gasifier and the hydrocarbon reforming reactor comprises feed to the methanol synthesis plant, such that a majority of the carbon dioxide ($CO_2$) produced by the biomass gasification reaction and the hydrogen ($H_2$) produced by the hydrocarbon reforming reactor are synthesized into methanol.

Biomass gasifiers are used to convert a variety of solid type biomass feedstocks to synthesis gas containing carbon monoxide and hydrogen that is used as feed to other chemical conversion processes. Biomass also contains low quantities and trace amounts of impurities that result in undesirable by-product gases, most notably carbon dioxide (an acid component), hydrogen sulfide (a sour component) and residual volatile organic compounds. To clean and prepare the raw gas so it is useable for catalytic conversion processes such as methanol and Fischer-Tropsch processes, the raw gas must be conditioned by removing the undesirable components in complex and capital intensive processing systems that require large amounts of energy and operating costs. In addition, associated large volumes of $CO_2$ greenhouse gas are produced that requires disposition to comply with emissions requirements, often making process economics unviable.

Reaction products out of a biomass gasification reaction typically contain carbon monoxide ($CO$), hydrogen ($H_2$), carbon dioxide ($CO_2$), ash and additional gases. Out of the biomass gasifier the effluent gases, known as synthesis gas (syngas), containing the $CO$, $H_2$, $CO_2$, additional gases and ash, may be quenched to a temperature such as less than 400° C. to stabilize the resulting gas molecules, filtered such that ash particles are removed from the syngas and then compressed to increase pressure to prepare the syngas for methanol ($CH_3OH$) synthesis. The syngas containing at least the $CO$, $H_2$ and $CO_2$ in the proper ratio can then be fed directly to a methanol synthesis unit for converting these gases to $CH_3OH$ via catalytic conversion.

One way of utilizing a biomass decomposition reaction for generating syngas for methanol synthesis includes an acid gas removal step located downstream of the quench and filtration steps and upstream the methanol synthesis plant. This acid gas removal step is utilized to remove CO2 and sulfur compounds from the syngas prior to feed to the methanol process.

This methanol synthesis process can use the more traditional synthesis process in which one mole of CO and two moles of H2 are reacted over the catalyst to produce CH3OH. Additionally, the methanol synthesis process, in the presence of significant amounts of CO2 and H2, may also use a process where one mole of CO2 and three moles of H2 are reacted over the catalyst to produce CH3OH plus H2O in conjunction with the traditional process.

In the latter case the CO2 in the syngas is reacted to create additional methanol and further increase the amount of carbon from the original biomass that is converted to methanol. This process, in conjunction with utilizing low sulfur containing woody biomass, eliminates any need for an acid gas removal step between the quench unit and the methanol synthesis plant to remove CO2 and/or sulfur as is necessary in conventional biomass decomposition reactions generating syngas for methanol synthesis. This process cuts down on CO2 emissions from the plant and instead uses that CO2 to create additional methanol.

One way of configuring a process utilizing a biomass decomposition reaction for generating syngas from biomass feedstock for methanol synthesis. The biomass is converted to CO, H2, CO2, ash and additional gases via a decomposition reaction such as gasification. A quench system to cool the gases to a temperature such as less than 400° C. to stabilize the resulting gas molecules and a filtration system to remove ash particles from the system are included in this gasification block. The syngas is then fed to a water-gas shift unit in which it is reacted over a catalyst to increase the H2:CO ratio to the ideal ratio for conventional methanol synthesis via the following reaction:

$$H_2O + CO \rightleftarrows H_2 + CO_2 \quad \text{(Reaction 1)}$$

For each mole of H2 produced in this reaction a mole of CO is converted to CO2. This is a key point because the syngas is then run through an acid gas removal unit in which primarily CO2 is removed to reduce the H2 demand, and the need for further water-gas shift, by limiting the CO2 passing through to the methanol synthesis unit. In addition sulfur compounds are removed to protect the methanol catalyst from being poisoned. The resultant syngas is then considered optimal for conventional methanol production and is fed to the methanol synthesis unit in which the following reactions occur:

$$2H_2 + CO \rightarrow CH_3OH \quad \text{(Reaction 2)}$$

$$3H_2 + CO_2 \rightarrow CH_3OH + H_2O \quad \text{(Reaction 3)}$$

The syngas feed to a conventionally operated methanol synthesis unit is greater than 90% H2 and CO with an H2:CO ratio of ~2. Less than 3% of the syngas feed is CO2 so as to limit the need for additional hydrogen. Therefore, Reaction 2 is by far the dominant methanol production reaction. This conventional configuration of a biomass decomposition and methanol synthesis process leads to a great deal of valuable biomass carbon being lost as CO2. This result is a lower methanol product yield and a higher carbon footprint. What is needed, therefore, is an integrated plant that improves carbon utilization of carbon molecules from gasified biomass such that a majority of the carbon dioxide and the hydrogen produced are synthesized into methanol.

Figure 1:
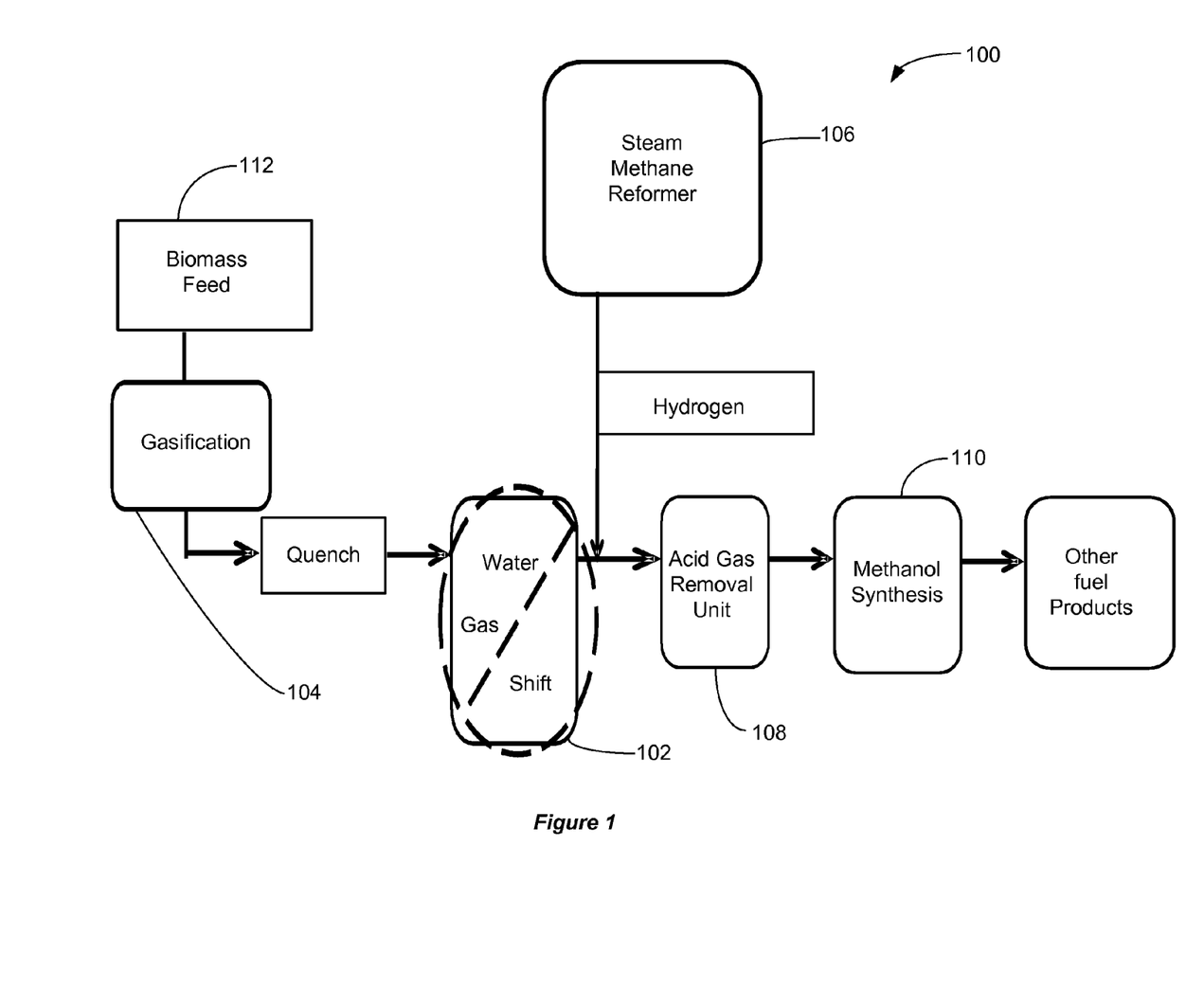
FIG. 1 is a flow sheet illustrating one embodiment of a biomass decomposition reaction for generating syngas from biomass feedstock for methanol synthesis according to the design.

FIG. 1 is a flow sheet illustrating one embodiment of a biomass decomposition reaction 100 for generating syngas from a biomass feedstock 112 for methanol synthesis. In this modified process configuration a water-gas shift unit 102 is excluded and instead H2 is added downstream of a gasification unit 104 to adjust the H2:CO ratio so that it is ideal for conventional methanol synthesis. To supply the added H2, a conventional hydrogen plant is included in the form of a Steam Methane Reformer 106 to produce hydrogen via natural gas reaction with steam over a steam-methane reforming catalyst.

By adding hydrogen to the syngas produced via gasification as opposed to utilizing the water-gas shift unit 102 for H2:CO ratio adjustment, CO in the syngas is not converted to CO2 via the water-gas shift reaction and therefore less biomass derived carbon is lost as CO2 in a acid gas removal unit 108. This result is greater total syngas feed to a methanol synthesis unit 110 and therefore greater methanol production for the overall process and the carbon footprint is smaller as compared with conventional processes, and is characterized by a lower emission of CO2 produced from biomass carbon.

Figure 2:
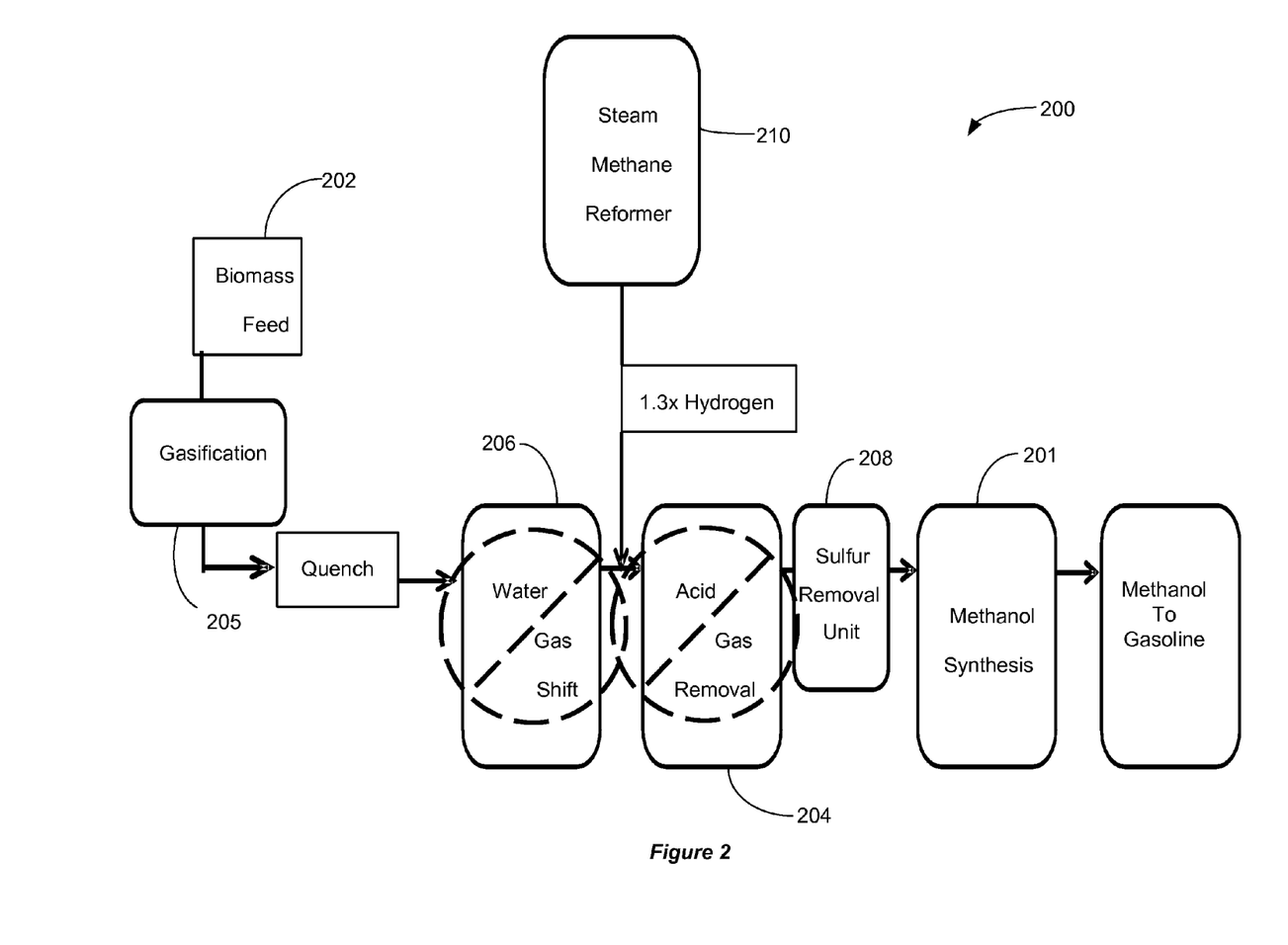
FIG. 2 is a flow sheet illustrating one embodiment of a biomass decomposition reaction for generating syngas from biomass feedstock for methanol synthesis in accordance with the design.

FIG. 2 is a flow sheet illustrating one embodiment of a biomass decomposition reaction 200 for generating syngas from biomass feedstock 202 for methanol synthesis 201. In the illustrated embodiment of FIG. 2, a modification to the conventional configuration utilizing a biomass decomposition reaction for generating syngas from biomass feedstock for methanol synthesis. In the configuration of FIG. 2, a acid gas removal (AGR) unit 204 and a water-gas shift unit 206 are no longer needed; the sulfur removal function of the acid gas removal unit 204 is replaced by a sulfur removal unit 208. The sulfur recovery unit 208 may be comprised of one or more sulfur guard fixed beds, an amine unit, or a combination, configured to remove sulfur and other gas contaminants from the combined syngas mixture. A greater amount of hydrogen is added downstream of gasification 205 so that the syngas hydrogen concentration is sufficient for reaction with both the CO and CO2 over the methanol synthesis catalyst. The required hydrogen is produced by a Steam Methane Reformer via a natural gas reaction with steam over a steam-methane reforming catalyst.

By adding hydrogen to and not removing CO2 from the syngas produced via gasification 206 both the reactions of CO and CO2 with H2 to produce methanol (Reaction 2 and Reaction 3, respectively) are accommodated. In this case, an example syngas stream may be ~70% H2, ~18% CO and ~11% CO2. By utilizing the biomass derived carbon in syngas present in both CO and CO2 forms, the result is even greater total syngas feed to the methanol synthesis unit 201 than in the process of FIG. 1, and therefore even greater methanol production overall. Thus, the carbon footprint is smaller as compared with the conventional processes and the configuration of FIG. 1, due to even lower emission of CO2 produced from biomass carbon.

In one exemplary embodiment, a biomass gasifier 205 comprises a radiant high heat-flux reactor configured to react woody biomass, received from the biomass feed system 202, in moist fine particle form at a temperature of at least 950 degrees C. The biomass gasifier 205 has a steam supply input and one or more heat sources. In the presence of the steam, the woody biomass in moist fine particle form is reacted in the radiant high heat-flux reactor in a rapid biomass gasification reaction to produce at least syngas components, including hydrogen (H2), carbon dioxide (CO2), and carbon monoxide (CO). Operating in parallel with the biomass gasifier 205 is a hydrocarbon reforming reactor 210 which is configured to receive a methane-based gas. The hydrocarbon reforming reactor 210 and the biomass gasifier 205 produce a high quality combined syngas mixture for methanol synthesis. The hydrocarbon reforming reactor 210 provides 1) hydrogen gas, 2) a hydrogen-rich syngas composition, in which a ratio of hydrogen (H2) to carbon monoxide (CO) is higher than a ratio generally needed for methanol synthesis, and 3) any combination of the two. The reaction products from the hydrocarbon reforming reactor 210 are mixed with a potentially carbon dioxide (CO2) rich syngas composition produced by the biomass gasifier 205, in which a ratio of hydrogen to carbon dioxide (H2:CO2) is higher than the ratio generally needed for methanol synthesis in order to convert greater than 60% of the carbon-based molecules in the woody biomass received from a biomass feed system into methanol by way of a methanol synthesis plant.

In one embodiment, the radiant high heat-flux reactor is configured to react woody biomass in the moist fine particle form in the rapid biomass gasification reaction at a temperature of at least 950 degrees C. primarily by way of a radiant heat emitted from the radiant high heat-flux reactor to produce reactant products including ash and syngas components of hydrogen and carbon monoxide exiting the radiant high heat-flux reactor. In another embodiment, the radiant high heat-flux reactor is configured to react the woody biomass received from the biomass feed system 202 in an oxidation free environment to produce the syngas components, including hydrogen (H2), carbon dioxide (CO2), and carbon monoxide (CO), where the carbon dioxide (CO2) comprises less than 50% by volume of the syngas.

In an exemplary embodiment, the hydrocarbon reforming reactor 210 is a Steam Methane Reformer (SMR), where biomass gasifier 205 has the biomass feed system 202, a first steam supply inlet, a first set of sensors to measure a chemical composition of produced product gases from the biomass gasifier 205, and a gasifier reactor control system to cause the biomass gasification reaction of the woody biomass in moist fine particle form at a temperature of at least 950 degrees C. The SMR reactor 210 has a methane-based gas feed system, a second steam supply inlet, a second set of sensors to measure a chemical composition of produced product gases from the SMR reactor, and an SMR control system. Both the SMR control system and the gasifier reactor control system are part of one or more control systems, wherein the gasifier reactor control system and the SMR control system interact to control an amount of hydrogen (H2) and carbon monoxide (CO) gases supplied to the combined syngas mixture to achieve a proper ratio of hydrogen (H2) to carbon monoxide (CO)) that is higher than a ratio generally needed for methanol synthesis. The higher ratio is obtained from 1) a first stream of the syngas components from the SMR reactor, 2) a separate second stream of the syngas components from the high radiant high heat-flux reactor and 3) a flow of hydrogen gas from a separator off a purge gas line coming out of the methanol synthesis plant, and any of these three sources are mixed together prior to feeding the combined syngas mixture at the proper ratio into the methanol synthesis plant.

In one embodiment, the hydrocarbon reforming reactor 210 is configured to supply a volume of hydrogen (H2) to the combined syngas mixture such that a ratio of the hydrogen to the sum of the carbon monoxide and the carbon dioxide (H2:(CO+CO2)) of the combined syngas mixture is between 2.1 and 2.8. In another embodiment, the hydrocarbon reforming reactor 210 is configured to supply a volume of hydrogen (H2) to the combined syngas mixture such that a majority of the carbon dioxide (CO2) entering the methanol synthesis plant is utilized in the synthesis of methanol. In still another embodiment, the hydrocarbon reforming reactor 210 may be configured to supply a quantity of hydrogen (H2) to the combined syngas mixture such that an exit flue gas from the methanol synthesize plant contains less than 3% of a total quantity of carbon-based molecules fed into the biomass gasifier. In yet another embodiment, the hydrocarbon reforming reactor 210 may be configured to supply the quantity of hydrogen (H2) to the combined syngas mixture such the combined syngas mixture such that most of a total quantity of carbon-based molecules fed into the biomass gasifier are converted into methanol and subsequently gasoline. Thus, less than 9% of the total quantity of carbon-based molecules fed into the biomass gasifier are not converted into gasoline (i.e. >91% conversion). In another embodiment, greater than 75% of the total quantity of carbon-based molecules fed into the biomass gasifier are converted per the table in FIG. 3.

In one embodiment, the detectors are configured to perform chromatography so as to measure the sulfur content of the woody biomass and ensure that the minimized sulfur content of the woody biomass is less than the 0.05% by dry weight of the woody biomass. The woody biomass in moist fine particle form is characterized by a decreased particle size and an overall increase in surface area due to being processed in the steam explosion unit. In another embodiment, the detectors may be configured to work in conjunction with a stored database which maintains a listing of all those certain varieties of trees that are suitable for creating woody biomass. The stored database lists at least a sulfur content and geographical location for each variety of tree, such that the woody biomass feed produced from each variety of tree possesses the minimized sulfur content of less than the 0.05% by dry weight of the woody biomass. In still another embodiment, the detectors that ensure the minimized sulfur content of less than the 0.05% by dry weight of the woody biomass further ensure that the woody biomass to be fed for the biomass gasifier possesses a minimized sulfur content of less than 0.01% by dry weight of the woody biomass.

In an exemplary embodiment, a sulfur removal unit is configured to remove at least sulfur-based gas contaminants from the syngas coming from the radiant high heat-flux reactor. The sulfur removal unit is downstream of the biomass gasifier and the hydrocarbon reforming reactor and are upstream of the methanol synthesis plant. In another embodiment, the sulfur recovery unit may be comprised of one or more sulfur guard fixed beds, or an amine unit, or a combination and configured to remove sulfur and other gas contaminants from the combined syngas mixture.

Figure 3:
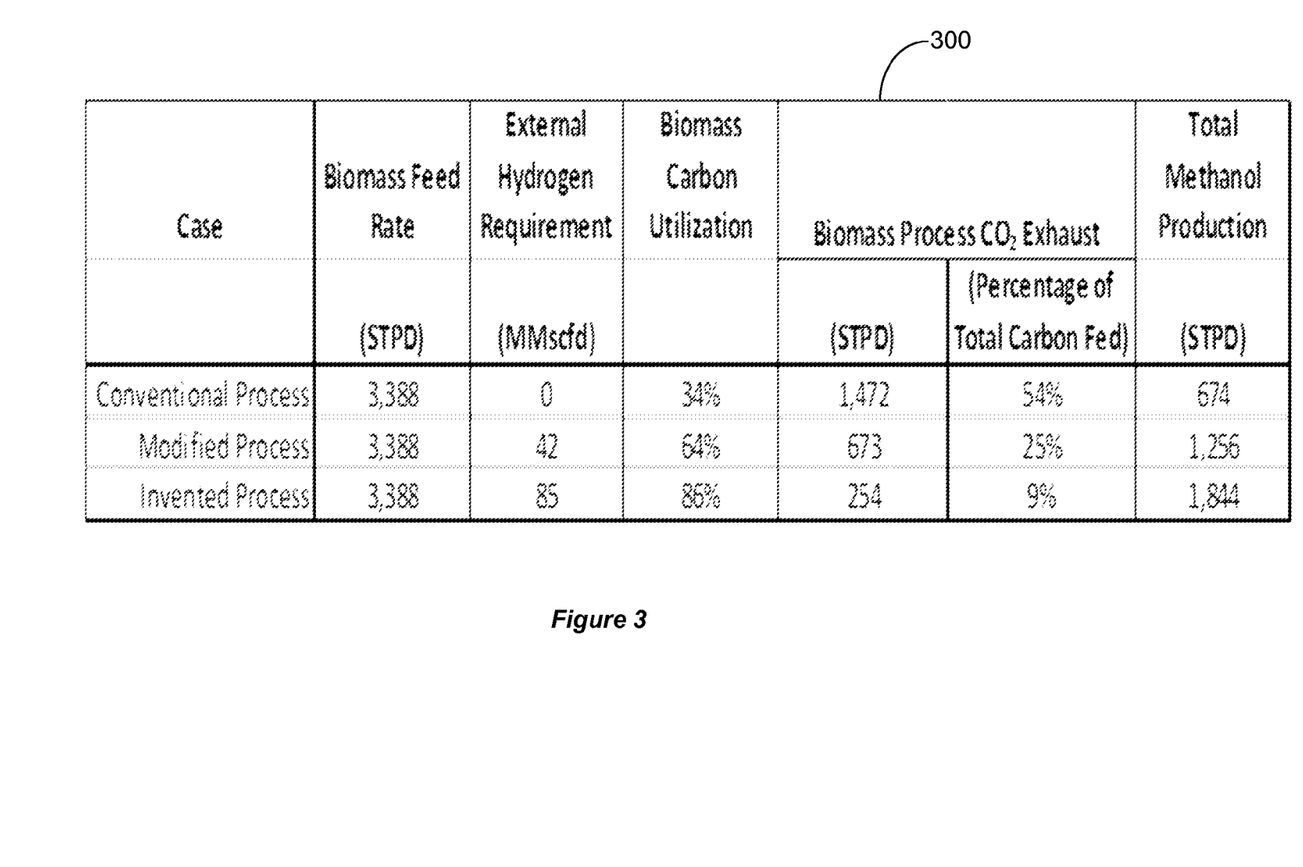
FIG. 3 is a table illustrating various performance parameters of an embodiment of a biomass decomposition reaction for generating syngas from biomass feedstock for methanol synthesis according to the design.

FIG. 3 is a table 300 illustrating various performance parameters of an embodiment of a biomass decomposition reaction for generating syngas from biomass feedstock for methanol synthesis according to the design. In the table 300 of FIG. 3, it is readily apparent that the process described in connection with FIG. 2 has greater methanol production, greater biomass carbon utilization and lesser biomass carbon emission as CO2 than either of the other described processes.

The process 200 described in connection with FIG. 2 may use low sulfur containing woody biomass to eliminate any need for an acid gas removal unit 204 between a quench unit of the gasifier 205 and the methanol synthesis plant 201 to remove CO2 and/or sulfur from typical hydrocarbon decomposition reactions generating syngas for methanol synthesis. The process 200 cuts down on CO2 emissions from the plant and instead uses that CO2 to create additional methanol. The process 200 increases use of carbon from the biomass. The combination of low sulfur naturally being in this type of woody biomass and low enough CO2 levels that the AGR unit 204 may be removed.

Syngas is passed for methanol synthesis. Methanol may then be stored for later methanol to gasoline conversion. In various embodiments, synthesis gas may be feed to another technical application. Examples include a syngas to another chemical conversion process, such as liquefied fuels used as transportation liquefied fuels. Some transportation liquefied fuels include jet fuel, DME, gasoline, diesel, and mixed alcohol, bio-char with a high sequestered amount of carbon; chemical production, electricity generation, synthetic natural gas production, heating oil generation, and other similar syngas based technical applications. In an example hydrocarbon based fuel, e.g., methanol, may be formed from syngas. The methanol may be further converted to gasoline or other fuels and various products may be separated out from the gasoline or syngas. These products, e.g., gasoline, may then be stored for later use as an energy source.

In one exemplary embodiment, the biomass feed system 202 comprises a steam explosion unit comprising an input cavity to receive woody biomass as a feedstock. The steam explosion unit further comprises one or more steam supply inputs, and two or more stages to pre-treat the woody biomass for subsequent supply to the biomass gasifier. The two or more stages use a combination of heat, pressure, and moisture that are applied to the woody biomass to make the woody biomass into the moist fine particle form. A steam explosion process breaks down a bulk structure of the received woody biomass, at least in part, by applying low-pressure steam through a first steam supply input to begin degrading bonds between lignin and hemi-cellulose from cellulose fibers of the woody biomass and increase a moisture content of the received woody biomass. Then, high-pressure steam is applied by way of a second steam supply input at a pressure of at least ten times atmospheric pressure to heat and pressurize any gases and fluids present within the woody biomass. The pressurized woody biomass is then rapidly depressurizing such that the increased moisture content and degraded bonds of the woody biomass internally blow apart the bulk structure of the woody biomass, thereby placing the woody biomass into the moist fine particle form. The woody biomass in the moist fine particle form is subsequently fed to a feed section of the biomass gasifier 205.

Figure 4:
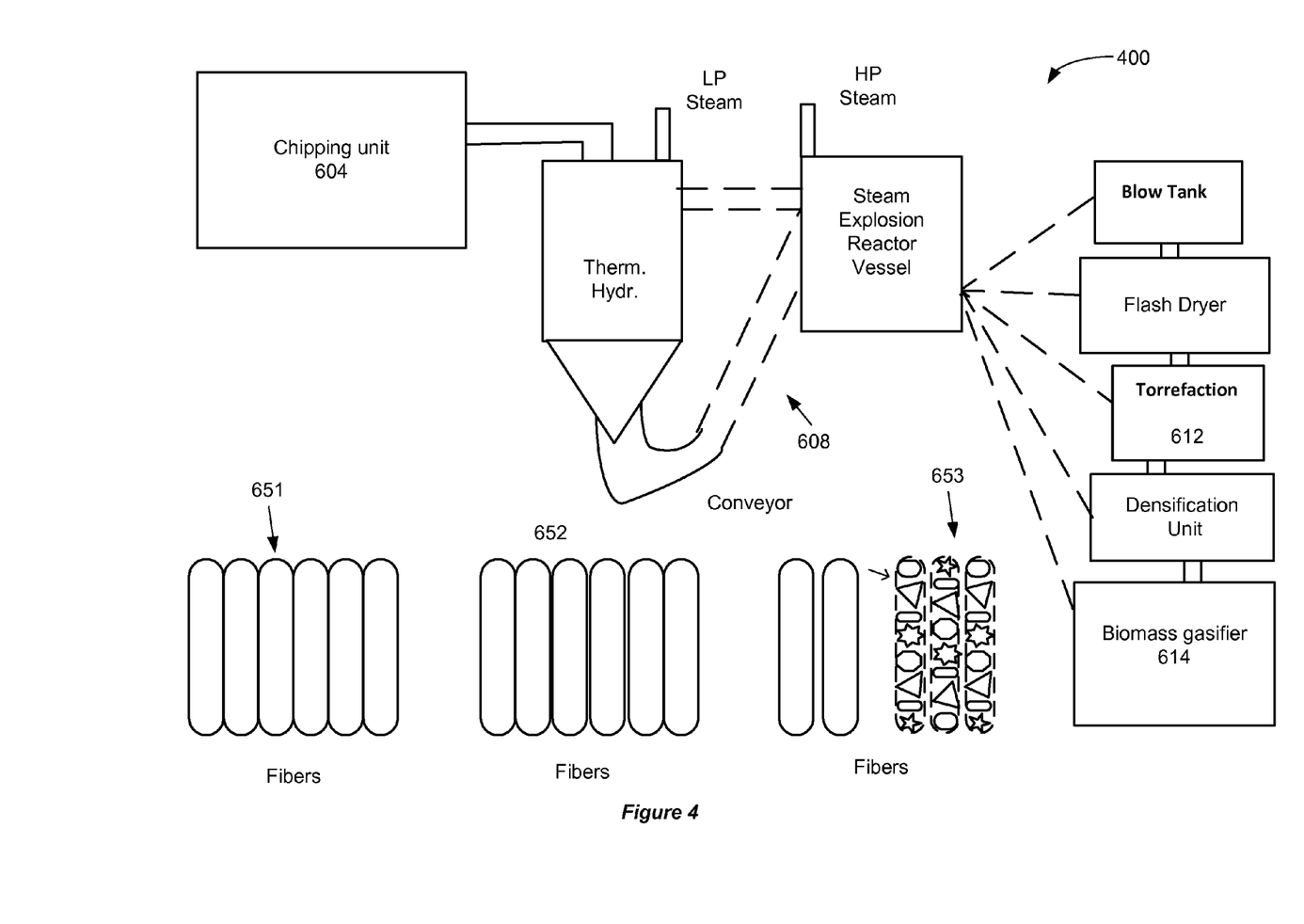
FIG. 4 illustrates a flow schematic of an embodiment of a steam explosion unit in accordance with the design.

A Steam Explosion Process (SEP) 608, a Thermal Mechanical Process (TMP), or other process may be used to form the woody biomass into particles for feeding into the biomass gasifier 205 to change the woody biomass into syngas. FIG. 4 illustrates a flow schematic of an embodiment of a steam explosion unit 400 having an input cavity to receive biomass as a feedstock, two or more steam supply inputs, and two or more stages to pre-treat the biomass for subsequent supply to a biomass gasifier 614 and/or torrefaction unit 612.

The steam explosion process 608 applies steam to the biomass in chip form 651 received in an input stage from a lower pressure steam supply input to begin degrading bonds between the lignin and cellulose fibers of the biomass and increase a moisture content of the biomass in chip form 651. Next, in another stage, the SEP process 608 applies a higher pressure steam at a pressure of at least ten times atmospheric pressure to heat and pressurize any gases and fluids present inside the biomass in order to internally blow apart the bulk structure of the biomass via a rapid depressurization of the biomass with the increased moisture content and degraded bonds.

In an embodiment, the thermally hydrating stage has low pressure steam applied to the biomass received in chip form 651 in order to soften and elevate a moisture content of the biomass so at least the cellulose fibers and surrounding lignin of the biomass in the steam explosion stage can be internally blown apart in the next stage. The biomass in chip form 651 in the thermally hydrating stage is heated to greater than 60° C. using the low pressure steam, and in the steam explosion stage, the softened and hydrated biomass is exposed to 160 to 850 PSI and temperature between 160-270° C. for a sufficient time period to create high pressure steam/fluid inside the partially hollow cellulose fibers and other porous areas in the bulk structure of the biomass material. In an embodiment, chips of biomass are heated to temperatures over 200° C. and pressures over 15 bar 23 bar (225 325 psi). The higher the pressure tends to create smaller fragments of lignin and cellulose fibers. In addition, when mechanical agitation is applied to the biomass as the biomass proceeds through the SEP process 608, this factor also tends to create smaller fragments of lignin and cellulose fibers when the biomass composition exits the steam explosion stage.

The pressure at an exit in the steam explosion stage is dropped rapidly in less than three seconds by extruding the bulk structure of the biomass into a tube at normal atmospheric pressure to cause an internal explosion, which internally blows apart the biomass into minute fine particles of biomass 653.

As shown in the diagram on the bottom of the figure, the biomass in fine particle form 653 formed after the pretreatment step of the steam explosion process is a fragment of one to several cellulose fibers adhering to each other with having some lignin on the fiber while other areas of the individual cellulose fibers have no lignin adhering to the surface of the cellulose fiber. Note, the biomass composition formed after the pretreatment step is generally individual cellulose fibers or even several cellulose fibers clumped together; however, merely a portion of the cellulose fibers remain intact, which makes the mass of each biomass particle smaller. The biomass composition formed after the SEP pretreatment step is multiple fragments of the individual cellulose fibers or even several cellulose fibers clumped together. The flow characteristics of these fragments of biomass in particle form 653 is more like that of grains of sand rather than like fiber stalks.

The biomass produced into the moist fine particle form 653 from the stages may have average dimensions of less than 50 microns thick and less than 500 microns in length. In an embodiment, the average dimensions of the particles of biomass produced from the steam explosion process are approximately 10 5 to 100 microns thick preferably 205-50 microns thick with a length of less than 200 microns (outliers may be up to 500 microns long), and the produced biomass in a particle form 653 has a length to thickness aspect ratio on average of less than 10 to 1. An aggregate amount of biomass in particle form 653 produced after the SEP pretreatment step has an increased exposed surface area of at least 20 times the surface area compared to a surface area of a same amount of biomass in chip form 653 supplied to an input stage of the SEP pretreatment step. The thickness of a single cell of biomass depending on the plant species is around 20 to 40 microns thick. Thus, the steam explosion process is generally blowing apart each cell in the biomass creating a small thickness of 5 to 20 microns thick for the resulting fine particles of biomass produced from the SEP.

Note, the lower the pressure in the steam explosion reactor vessel, such as (6 bar), the bigger the particles of biomass are formed almost like fiber particles; and likewise, the higher the pressure in the steam explosion reactor vessel, such as (16 bar), the smaller the particles of biomass are formed almost like fine grains of sand or finely ground up coffee grounds.

The increased surface area of the resulting fine particles of biomass formed as a product of the SEP also can improve the downstream biomass gasifier's performance. The SEP produces a higher amount of surface area for a same starting quantity of biomass than the TMP process on the biomass. The higher amount of surface area makes a higher throughput of biomass material attainable through the same biomass gasifier design. The reaction rate of biomass particles passing through the biomass gasifier in the biomass gasification reaction seems to be a mathematical function of the surface area of those fine particles biomass. A steam oxidation of the biomass occurs in the biomass gasification reaction. The steam oxidation of the biomass affects the reaction rate of the biomass particles in the biomass gasification reaction. Thus, a higher throughput is attainable with the increased reaction rate due to the greater surface area of the produced fine particles of biomass from SEP. The higher throughput results in any of 1) a lower residence time is needed in the biomass gasifier for a same amount of SEP biomass particles compared to a TMP biomass particle size; and alternatively, 2) a higher quantity of SEP biomass particles can be reacted in the biomass gasifier compared to a TMP biomass particle size for a same amount of residence time in the biomass gasifier.

Those produced moist fine particles of biomass 653 can be subsequently fed to a feed section of the biomass gasifier 614, the torrefaction unit 612, a densification unit, a dryer, or any combination of these. Note, the produced moist fine particles of biomass 653 can be directly fed to a feed section of the biomass gasifier 614 after passing through a dryer/low temperature 300 degree C. torrefaction unit and obtaining the desire moisture content for the biomass gasifier.

The internally blowing apart the bulk structure of biomass in a fiber bundle into pieces and fragments of cellulose fiber, lignin and hemi-cellulose results in all three 1) an increase of a surface area of the biomass in fine particle form compared the received biomass in chip form 651, 2) a creation of the two step reaction in the biomass gasification reaction of any of lignin adhering cellulose fiber as well as any loose chunks of lignin and then a reaction of the cellulose fibers as opposed to a multistep cycling reaction of lignin and then the cellulose fibers followed by lignin and more cellulose fibers, and 3) a change in viscosity of the resulting produced biomass in fine particle form 653 to flow like grains of sand rather than like fibers.

TMP and SEP are two methods discussed for producing the biomass in particle form. Other methods for producing these chunks of lignin and lignin-coated fibers are generally regarded as high yield pulping processes. One of these includes what is known as Chemi-Thermo Mechanical Pulp (CTMP). In this process sodium sulfite is added to help loosen the lignin. Grinding the chips in a stone mill may also be used. These fibers are known as stone ground wood.

Both the steam explosion unit 608 and the TMP process are configured to receive two or more types of biomass feed stocks, where the different types of biomass include 1) soft woods, 2) hard woods, 3) grasses, 4) plant hulls, and 5) any combination that are blended. The steam explosion process or TMP turns them into a homogenized feedstock that is subsequently collected and then fed into the biomass gasifier 614, or torrefaction unit 612. The torrefaction unit 612, and biomass gasifier 614 are designed to be feedstock flexible without changing out the physical design of the feed supply equipment or the physical design of the biomass gasifier or torrefaction unit via at least particle size control of the biomass particles produced from steam explosion stage or TMP process.

After the thermally hydrating stage, the softened biomass in chip form 651 are any combination of 1) crushed and 2) compressed into a plug form, which is then fed into a continuous screw conveyor system, which these provide a mechanical agitation to the biomass to be combined with the high pressure steam explosion used in this SEP process. The continuous screw conveyor system moves the biomass in plug form into the steam explosion stage. The continuous screw conveyor system also uses the biomass in plug form to prevent blow back backpressure from the high-pressure steam present in the steam explosion stage from affecting the thermally hydrating stage. Other methods could be used such as 1) check valves and 2) moving biomass in stages where each stage is isolatable by an opening and closing mechanism.

The steam explosion stage can operate at pressures up to 850 psi. The plug screw feeder conveys the chips along the steam explosion stage. High-pressure steam is introduced into the plug screw feeder in a section called the steam mixing conveyor. The high pressure supply input may consist of several nozzles strategically placed around the steam mixing conveyor. Retention time of the biomass chip material through the steam explosion stage is accurately controlled via the plug screw feeder. In the steam explosion stage, the biomass in plug form is exposed to high temperature and high pressure steam at a temperature of at least 160 degree C. and 160 PSI from the high pressure steam input for at least 5 to 15 minutes and preferably around 10 minutes until moisture penetrates porous portions of the bulk structure of the biomass and all of the liquids and gases in the biomass are raised to the high pressure.

The continuous screw conveyor system feeds the biomass in plug form through the steam explosion stage to an exit. In an embodiment, a small opening forms the exit, such as ½ to ¾ inch opening, and goes into a tube that is maintained at around atmospheric pressure and any internal fluids or gases at the high pressure expand to internally blow apart the biomass. The pressure at the exit in the steam explosion stage is dropped rapidly by extruding the bulk structure of the biomass at between 160 to 850 PSI into a tube at normal atmospheric pressure to cause an internal "explosion" rapid expansion of steam upon the drop in pressure or due to the "flashing" of liquid water to vapor upon the drop in pressure below its vapor pressure, which internally blows apart the biomass in chip form 651 into minute fine particles of biomass 653. In another embodiment, the steam explosion reactor portion of the steam explosion stage contains a specialized discharge mechanism configured to "explode" the biomass chip material to a next stage at atmospheric pressure. The discharge mechanism opens to push the biomass from the high-pressure steam explosion reactor out this reactor discharge outlet valve or door into the feed line of the blow tank. Thus, the pressurized steam or super-heated water out of the steam explosion reactor in this stage is then dropped rapidly to cause an explosion, which disintegrates the chips of biomass into minute fine particles. The original bundle of fibers making up the biomass is exploded into fragments making discrete particles of fine powder.

The moisture and biomass chips get extruded out the reactor discharge to a container, such as the blow line, at approximately atmospheric pressure. The size of the exit orifice effects factors such as exit velocity, a depressurization time constant, and even whether every fiber exiting mechanically interacts with an edge of the orifice or has enough space to violently interact with the other mass around that fiber but not too much to space such as a 3 inch exit orifice to allow many fibers to exit without violently interacting with a neighboring fiber or edge of the exit orifice line. Thus, the size of the exit orifice is controlled relative to the size of the fibers passing through that exit orifice. The high-pressure steam or water conversion to vapor inside the partially hollow fibers and other porous areas of the biomass material causes the biomass cell to explode into fine particles of moist powder. The bulk structure of the biomass includes organic polymers of lignin and hemi-cellulose that surrounds a plurality of cellulose fibers. The bulk structure of the biomass is internally blown apart in this SEP step that uses at least moisture, pressure, and heat to liberate and expose the cellulose fibers to be able, as an example, to directly react during the biomass gasification reaction rather than react only after the layers of lignin and hemi-cellulose have first reacted to then expose the cellulose fibers. The high temperatures also lowers the energy/force required to breakdown the biomass' structure as there is a softening of lignin that facilitates fiber separation along the middle lamella.

The morphological changes to the biomass coming out of SEP reactor can include: 1) no intact fiber structure exists rather all parts are exploded causing more surface area, which leads to higher reaction rates in the biomass gasifier; 2) fibers appear to buckle, they delaminate, and cell wall is exposed and cracked; 3) some lignin remains clinging to the cell wall of the cellulose fibers; 4) hemi-cellulose is partially hydrolyzed and along with lignin are partially solubilized; 5) the bond between lignin and carbohydrates/polysaccharides (i.e. hemi-cellulose and cellulose) is mostly cleaved; and 6) many other changes as discussed herein.

The created moist fine particles may be, for example, 20-50 microns thick in diameter and less than 100 microns in length on average. Note, 1 inch=25,400 microns. Thus, the biomass comes from the chipper unit 104 as chips up to 1 inch in length and 0.25 inches in thickness on average and go out as moist fine particles of 20-50 microns thick in diameter and less than 100 microns in length on average, which is a reduction of over 2000 times in size. The violent explosive decompression of the saturated biomass chips occurs at a rate swifter than that at which the saturated high-pressure moisture in the porous areas of the biomass in chip form can escape from the structure of biomass.

Note, no external mechanical stripping of the fiber bundles is needed in SEP rather the process uses steam to explode cells from inside outward and potentially uses some mechanical agitation of the biomass to create smaller fragments as a resultant product. Use of SEP on the biomass chips produces small fine particles 653 of cellulose and hemi-cellulose with some lignin coating. This composite of lignin, hemi-cellulose, and cellulose in fine form has a high surface area that can be moved/conveyed in the system in a high density.

The produced fine particles of biomass are fed downstream to the biomass gasifier 614 for the rapid biomass gasification reaction in a reactor of the biomass gasifier 614 because they create a higher surface to volume ratio for the same amount of biomass compared to the received biomass in chip form 651, which allows a higher heat transfer to the biomass material and a more rapid thermal decomposition and gasification of all the molecules in the biomass.

The produced particles of biomass loses a large percentage of the moisture content due to steam flashing in the blow line and being vented off as a water vapor. The produced particles of biomass and moisture are then separated by a cyclone filter and then fed into a blow tank. Thus, a water separation unit is in line with the blow line. A collection chamber at an outlet stage of the steam explosion stage is used to collect the biomass reduced into smaller particle sizes and in pulp form and is fed to the water separation unit. Water is removed from the biomass in fine particle form in a cyclone unit or a flash dryer.

A moisture content of the fine particles of biomass 653 is further dried out at an exit of the blow tank by a flash dryer that reduces the moisture content of fine particles of biomass 653 to 5-20% by weight preferably and up to 35% in general. A goal of the fiber preparation is to create particles of biomass with maximum surface area and as dry as feasible to 5-20% moisture by weight of the outputted biomass fine particle. The flash dryer merely blows hot air to dry the biomass particles coming out from the blow tank. The flash dryer can be generally located at the outlet of the blow tank or replace the cyclone at its entrance to make the outputted biomass particles contain a greater than 5% but less than 35% moisture content by weight.

The resulting particles of biomass differs from Thermal Mechanical Pulping (TMP) in that particles act more like crystal structures and flows easier than fibers which tend to entangle and clump.

The reduced moisture content of 5% to about 35% by weight of the biomass in fine particle form is fed by a conveying system, as an example, to a torrefaction unit 612 to undergo torrefaction or pyrolysis at a temperature from 100 to 700 degrees C. for a preset amount of time.

A conveyor system supplies the biomass in particle form to a torrefaction unit 612 to process the biomass at a temperature of less than 700 degrees C. for a preset amount of time to create off gases to be used in a creation of a portion of the syngas components that are collected by a tank and may be eventually fed to the methanol synthesis reactor.

The fine particles of biomass 653 out of the blow tank and flash dryer has a low moisture content already due to the steam flashing, further air drying, and are a composite of fragments of cellulose fibers with a lignin coating, pieces of lignin, cellulose, and hemi-cellulose, etc. The biomass gasifier 614 has a reactor vessel configured to react the biomass in moist fine particle form with an increased surface area due to being blown apart by the steam explosion unit 608. The biomass gasifier 614 has a high pressure steam supply input and one or more heaters, and in the presence of the steam the biomass in fine particle form 653 are reacted in the reactor vessel in a rapid biomass gasification reaction between 0.1 and 5.0 second resident time to produce at least syngas components, including hydrogen ($H_2$) and carbon monoxide (CO). When the biomass in fine particle form 653 produced are supplied in high density to the biomass gasifier 114, then the small particles react rapidly and decompose the larger hydrocarbon molecules of biomass into the syngas components more readily and completely. Thus, nearly all of the biomass material, lignin, cellulose fiber, and hemi-cellulose, completely gasifies rather than some of the inner portions of the chip not decomposing to the same extent as that fine particle. These fine particles compared to chips create less residual tar, less carbon coating and less precipitates. Thus, breaking up the integrated structure of the biomass in a fiber bundle tends to decrease an amount of tar produced later in the biomass gasification. These fine particles also allow a greater packing density of material to be fed into the biomass gasifier 614. As a side note, having water as a liquid or vapor present at at least 10 percent by weight may assist in generating methanol $CH_3OH$ as a reaction product in addition to the CO and $H_2$ produced in the biomass gasifier 614.

In one embodiment, the torrefaction unit 612 and biomass gasifier 614 may be combined as an integral unit.

In the alternative, the moist blown apart particles of biomass may be fed in slurry form from the output of the steam explosion reactor directly, or after drying, to a densification unit. The densification unit may densify the biomass from form into pellets of biomass, which those pellets are then fed into the biomass gasifier 614. This direct feed and conversion of biomass from form to pellet form saves multiple steps and lots of energy consumption involved in those eliminated steps. Alternatively, the pellets may be transported to facilities for further processing to liquid fuel, heat/power, animal feed, litter, or chemicals.

In an embodiment, the biomass gasifier 614 is designed to radiantly transfer heat to particles of biomass flowing through the reactor design with a rapid gasification residence time, of the biomass particles of 0.1 to 10 seconds and preferably less one second. The biomass particles and reactant gas flow through the radiant heat reactor. Primarily radiant heat from the surfaces of the radiant heat reactor and particles entrained in the flow heat the particles and resulting gases to a temperature in excess of generally 700 degrees C. and preferably 1300° C. to produce the syngas components including carbon monoxide and hydrogen, as well as keep produced methane at a level of ≤1% of the compositional makeup of exit products, a resultant stable ash formation, complete amelioration of tar to less than 500 milligrams per normal cubic meter, and the production of the hydrogen and carbon monoxide products. In some embodiments, the temperature range for biomass gasification is greater than 800 degrees C. to 1400 degrees C. In some embodiments, the temperature range for biomass gasification is greater than 700 degrees C. to 1450 degrees C. In some embodiments, the temperature range for biomass gasification is greater than 1000 degrees C. The biomass in particle form used as a feed stock into the radiant heat reactor conveys the beneficial effects of more effective heat transfer of radiation to the biomass particles and increased gasifier yield of generation of syngas components of carbon monoxide and hydrogen for a given amount of biomass fed in, and improved process hygiene via decreased production of tars and C2+ olefins compared to chips of biomass. A control system for the radiant heat reactor matches the radiant heat transferred from the surfaces of the reactor to a flow rate of the biomass particles to produce the above benefits.

The biomass in particle form produced for fuel production breaks apart a larger piece of biomass into the particle sizes to increase an exposed surface area of the particles compared to the larger piece of biomass. The particle sizes compared to the larger piece of biomass increases surface area, improves flow characteristics because it flows more like grains of sands/coffee rather than like fibers, results in less tar and char formation in downstream torrefaction or gasifier process and rather decomposes more completely into constituent gases including CO, H2, CO2 and ash.

Another possible biomass gasifier 614 implementation has a high temperature steam supply input and one or more regenerative heaters. In the presence of the steam, the particles of the biomass broken down by the pretreatment step are reacted in the reactor vessel in a rapid biomass gasification reaction at a temperature of greater than 700 degrees C. in less than a one second residence time in the biomass gasifier to create syngas components, including hydrogen (H2) and carbon monoxide (CO). The biomass gasifier 614 can typically feed to a methanol (CH3OH) synthesis reactor.

Figure 5:
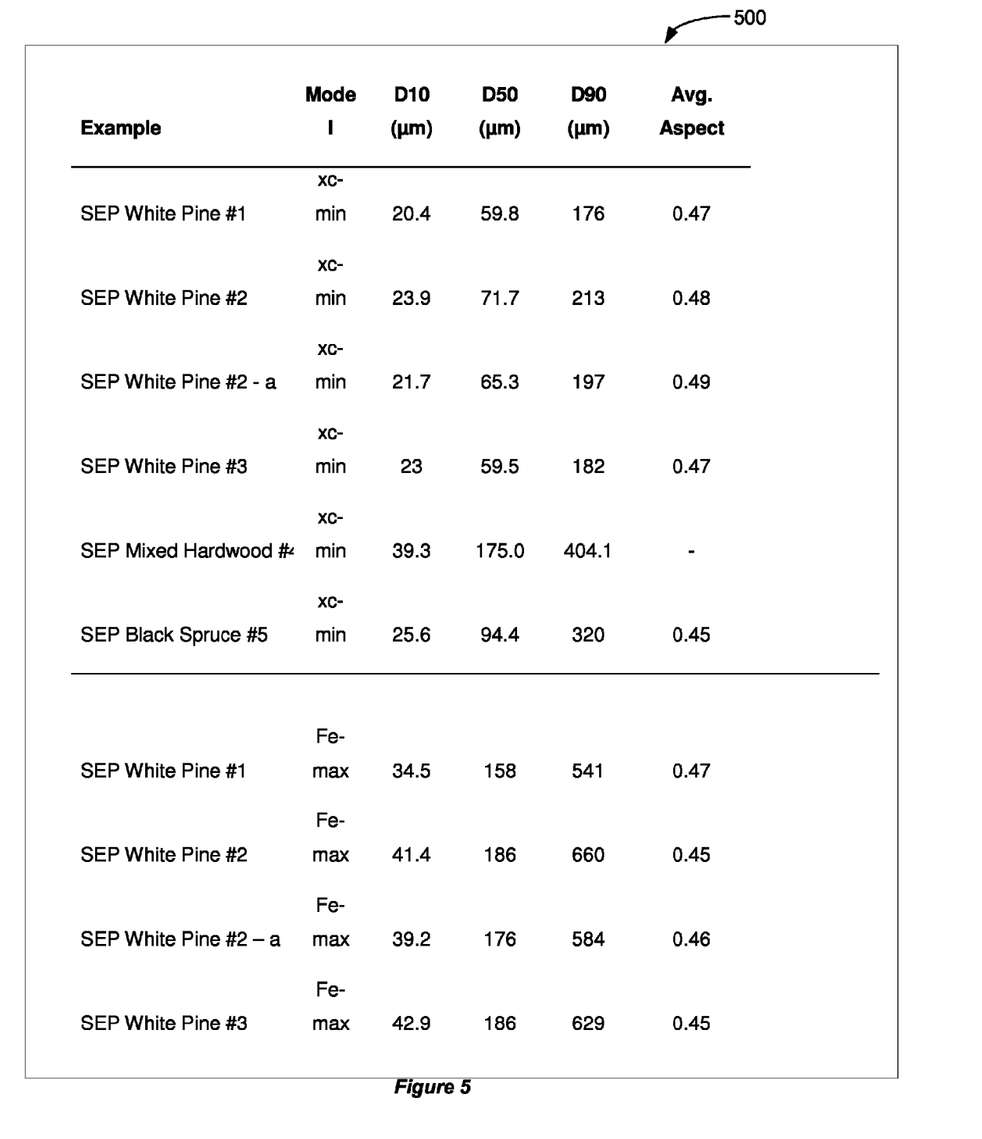
FIG. 5 is a table illustrating one embodiment of a particle size distribution obtained by steam exploding samples of different varieties of woody biomass.

FIG. 5 is a table 500 illustrating one embodiment of a particle size distribution obtained by steam exploding samples of different varieties of woody biomass. The samples illustrated in FIG. 5 were produced with a steam pressure of 16 bar and a reaction time of 10 minutes. An example Particle Size Analysis to determine the particle size can be a Digital Image Processing Particle Size and Shape Analysis System such as a Horiba Camsizer XT particle size analyzer. Such a system uses one or more cameras to provide rapid and precise particle size and particle shape distributions for dry powders and bulk material in the size range, for example, from 30 μm to 30 mm. The measurements from the digital image processing system allows a correlation to existing data from techniques as diverse as sieving and sedimentation, which in some instances may also be used to measure particle size. In an embodiment, the particle size of the steam exploded wood chips is measured using a Horiba Camsizer XT particle size analyzer. The sample to be measured is mixed in a resealable bag by kneading and agitating the material in the bag by external manipulation. After mixing, a sample amount, such as approximately 3 cm^3, is loaded into the sample hopper of the instrument. The target is to run and analyze enough sample size, such as at least 2 million particles from each sample, so the sample volume is only important insofar as it corresponds to an adequate number of particles. Example settings on the instrument can be as follows 0.2% covered area, image rate 1:1, with X-Jet, gap width=4.0 mm, dispersion pressure=380.0 kPa, xFe_max [and xc_min, accordingly]. Feed rate is controlled to yield a target covered area so that the computer can process the images quickly enough. The camera imaging rate is fixed, and both "basic" and zoom images are obtained for every run. A single value for average particle size, such as the diameter is less than 50 microns, may be the objective measurement standard. In an embodiment, a three point value for both Fe-max and xc-min is more complete. So that's like a 6 point value. The particle size distribution (PSD) may be defined as Fe-Max D10, D50, D90 and Xc-min D10, D50, D90. The measurement then can use multiple values such as input 6 values to determine the measurement. Other similar mechanisms may be used.

Calculations can be made using Fe max and xc min on a volume basis. Two models can be used to analyze the particle images: xc-min, which yields results comparable to those obtained by physically screening/sieving samples, and Fe-max, which is similar to measuring the longest dimension of a given particle with a caliper. Raw data, frequency plots, binned results, and particle images are obtained for all samples. D10, D50, and D90 may be calculated on a volume basis, as is the average aspect ratio. D90 describes the diameter where ninety percent of the distribution has a smaller particle size and ten percent has a larger particle size. The D10 diameter has ten percent smaller and ninety percent larger. A three point specification featuring the D10, D50, and D90 is considered complete and appropriate for most particulate materials. In an embodiment, the particle size distribution PSD may be defined as D50 (μm) Model Fe-max.

As discussed, the decomposition of the large carbohydrate and other organic molecules in the biomass gasification reaction occurs due to exposure of the biomass composition to elevated heat of greater than 700 degrees C., but not to an internal flame or other combustion source. Thus, an external heater heats the biomass in particle form. The exposure of the cellulose fibers to be able to directly react during the biomass gasification reaction rather than merely reacting only in a repeating cycle of the layer of lignin first reacting to then expose the cellulose fibers, and then a next layer of lignin followed by cellulose fibers reacting causes a biomass gasification reaction product of resultant stable ash formation, a complete amelioration of tar to less than 500 milligrams per normal cubic meter, and a yield of at least 90% of the biomass to hydrogen, carbon dioxide, and carbon monoxide gaseous products.

The biomass gasifier feeds a gas clean up section to clean ash, sulfur, water, and other contaminants from the syngas gas stream exiting the biomass gasifier 614. The syngas is then compressed to the proper pressure needed for methanol synthesis 201. The syngas from a catalytic converter may connect upstream or downstream of the compression stage.

The synthesis gas of H2 and CO from the gasifier 205 is sent to a common input to the one or more methanol synthesis reactors 201. The methanol produced by the one or more methanol synthesis reactors 201 is then processed in a methanol to gasoline process. The liquid fuel produced in the integrated plant may be gasoline or another such as diesel, jet fuel, or some alcohols.

Quenching, via an injection of cooling medium into the reaction products, may occur as well as gas clean up, and ash removal from the system. Direct quenching methods of cooling the hot reaction products via for example direct spraying of cooling mediums into the stream carrying the hot reaction products cause the cooling of the hot reaction products. Other example methods such as annular quenching methods of cooling the pipe carrying the hot reaction product from the biomass gasification reactor via heat transfer through the pipe are possible. Features described in one embodiment may be used in another embodiment.

The chemical plant may directly cool the reaction products from the effluent stream out of the biomass gasification reactor. One or more spray nozzles in the quench zone spray a liquid cooling fluid directly into the reaction product stream from the biomass gasification chemical reactor. The direct spraying of a liquid cooling fluid into the stream carrying the hot reaction products causes the liquid cooling fluid to vaporize into a superheated gas. The liquid cooling fluid, such as water, becomes a superheated vapor, such as superheated steam, extracting the energy from the hot reaction products.

A control system controls one or more of the following plant parameters to ensure the temperature is at or below 400 C when leaving the quench zone, where the control system 1) changes a flow rate of a cooling medium being sprayed into the hot reaction products, 2) provides feedback to change the flow rate of biomass into the biomass gasification chemical reactor, or 3) directs the reactor's heat source to change an amount of concentrated energy being inputted into the reactor.

Thus, the quench zone may form near an exit of a gasification reaction zone in the reactor tubes of the chemical reactor so as to not crack or not thermally affect the reactor tubes. Two or more of the multiple reactor tubes may form into a group at the exit and that group combines their reaction products and un-reacted particles from the biomass gasification into a larger tube per group that forms a portion of the quench zone or all of the tubes may supply the reaction products into a common manifold that forms a portion of the quench zone.

The one or more sprayers, such as valves and nozzles, located inside the quench zone inject the cooling fluid directly into the reaction product syngas stream to make the temperature transition from the at least 1000 degree C. to less than 400 degrees C. within the 0.1-10 seconds to further prevent metal dusting corrosion of the pipe walls and minimizes an amount of time for a water gas shift reaction to occur and generate CO2 as a byproduct.

A particle filter removal component downstream of the quench zone removes ash and other particles from the superheated gas and hot reaction products supplied from the quench zone. The particle filter may also remove some of the moisture content in the superheated gas. The particle filter may also remove some corrosive or otherwise undesired chemicals that could be damaging to the Rankine cycle engine. The hot reaction products and superheated gas can used as a medium to drive a Rankine cycle engine, such as a turbine, to draw the energy from the super heated vapor form of the cooling medium and hot reaction products. The Rankine cycle engine has an input to receive the hot reaction products and superheated gas. The super heated vapor form of the cooling medium and the hot reaction products after transferring their energy through the Rankine cycle change states to a saturated vapor heavy in moisture content. The Rankine cycle engine may be in line to receive the superheated gas vapor or connected to a heat exchanger, which extracts the majority of heat energy out of the super heated gas vapor.

Thus, the super heated vapor form of the cooling medium and hot reaction products after transferring their energy change states to a saturated vapor heavy in liquid. The saturated vapor heavy flow through one or more knock out drums to dry the vapor, which then can run an organic turbine in another Rankine cycle or transfer its energy via a steam condensing heat exchanger. Thus, the knockout drums located downstream of the Rankine engine remove entrained water or other moisture from the syngas stream supplied from the quench zone.

In an embodiment, the syngas must have total tar concentrations below 200 mg Nm-3, catalyst poison concentrations below 100 ppb for H2S, HC1, and NH3, and have a H2:CO ratio within the example range 2.3 to 2.7. These compositional concentration measurements will be taken periodically during gasifier operation through FTIR spectroscopy and gas chromatography periodically and measured with other detectors on a steady state basis. These parameters may be fed to the control system to ensure that synthesis gas composition does not vary (+/−10%) from the desired composition, as well as to verify that catalyst poison concentrations are not above deactivation thresholds for the methanol synthesis catalyst. Ash measurements will be made one or more times daily and mass balances will be performed to ensure that overall biomass conversion remains above threshold targets and that alkali deposits are not being formed on the inside of the reactor.

In an embodiment, a quench zone immediately downstream of an exit of the chemical reactor may be used to immediately quench via rapid cooling of at least the hydrogen and carbon monoxide reaction products. For example, the quench zone may be used to immediately and rapidly cool at least the hydrogen and carbon monoxide reaction products within 0.1-10 seconds of exiting the reactor to a temperature of 800 degrees C. or less and preferably 400 degrees or less. In an embodiment, quenching the hydrogen and carbon monoxide reaction products within 0.1-10 seconds of exiting the reactor to 500 degrees C. or less prevents metal dusting from occurring in most alloys. The quench zone generally rapidly cools the reacted biomass products from the gasification reaction as well as the resultant ash and un-reacted biomass. In some embodiments, the cooling might occur within 0.1-10 seconds of exiting the chemical reactor and cooling to a temperature of 400 degrees C. or less. Generally, 800 degrees C. is below a level to prevent the hydrogen and carbon monoxide reaction products from gasification reaction to revert back to other larger hydrocarbon compounds If not cooled by the immediate quench. Additionally, the quench may prevent coalescence of ash remnants of the biomass particles. The cooling to less than 400 degrees C. should prevent metal dusting. The syngas may also pass through light particle knockout drums, which may cool and clean the syngas gas stream to the appropriate temperature for the methanol synthesis.

Other filters might be used in addition to or in place of the stainless steel metal filters. For example, high temperature fabric filter or centrifugal cyclone filters, such as multiple stage cyclone filters, might also be used. The filters might be made of material to resist 400 degrees C. The filters, e.g., the centrifugal cyclone filters, might also be coated for abrasion reduction and corrosion resistance. The filters, e.g., the centrifugal cyclone filters might be located before the sulfur remediation unit. Additionally, such a filter may allow unreacted biomass recycling with cyclone separation, heavy cyclone stage to remove heavy particles and lighter cyclone stage to remove biomass to improve yields. Additionally, added metal oxide may allow the ash to be removed magnetically in some embodiments. Other types of filters that might also be used for ash removal include momentum change filters or abrupt changes in flow path filters, such as knock out drums. Additionally any combination of these filters might be used for ash removal.

In an embodiment, in a final step before synthesis of methanol, the gas is passed to a compressor set. The compressor directly feeds syngas to a methanol synthesis unit and brings the pressure to that required for methanol synthesis. For example, the pressure may be 750-1200 PSIG. The methanol synthesis unit may consist of one or more shell and tube Lurgi style methanol reactors.

While some specific embodiments of the design have been shown the design is not to be limited to these embodiments. For example, most functions performed by electronic hardware components may be duplicated by software emulation. Thus, a software program written to accomplish those same functions may emulate the functionality of the hardware components in input-output circuitry. The design is to be understood as not limited by the specific embodiments described herein, but only by scope of the appended claims.

The invention claimed is:

1. An integrated plant to improve carbon utilization of carbon molecules from gasified woody biomass to be converted into methanol, comprising:
a biomass gasifier comprising a radiant high heat-flux reactor configured to react woody biomass received from a biomass feed system in moist fine particle form at a temperature of at least 950 degrees C., where the biomass gasifier has a steam supply input and one or more heat sources, and in the presence of steam, the woody biomass in moist fine particle form is reacted in the radiant high heat-flux reactor in a rapid biomass gasification reaction to produce at least syngas components, including hydrogen (H2), carbon dioxide (CO2), and carbon monoxide (CO);
a hydrocarbon reforming reactor configured to receive a methane-based gas, where the hydrocarbon reforming reactor is in parallel to and cooperates with the radiant high heat-flux reactor to produce a high-quality combined syngas mixture for methanol synthesis between the resultant reactant products coming from the two reactors, wherein the hydrocarbon reforming reactor provides 1) hydrogen gas, 2) a hydrogen-rich syngas composition, in which a ratio of hydrogen (H2) to carbon monoxide (CO) is higher than a ratio generally needed for methanol synthesis, and 3) any combination of the two, to be mixed with a potentially carbon dioxide (CO2) rich syngas composition produced by the biomass gasifier, in which a ratio of hydrogen to carbon dioxide (H2:CO2) is higher than the ratio generally needed for methanol synthesis in order to convert greater than 60% of the carbon-based molecules in the woody biomass received from the biomass feed system into methanol by way of a methanol synthesis plant;
one or more detectors that are geographically located on the same site as the radiant high heat-flux reactor, wherein the one or more detectors are configured to measure a sulfur content of the woody biomass and are configured to ensure a minimized sulfur content of the woody biomass to less than 0.05% by weight such that the integrated plant operates without a water-gas-shift unit and without an acid gas removal unit because the methanol synthesis plant converts the carbon dioxide into methanol and the one or more detectors ensure that the woody biomass has a minimized sulfur content; and
a sulfur removal unit configured to remove at least sulfur-based gas contaminants from the syngas components coming from the radiant high heat-flux reactor, where the sulfur removal unit is downstream of the biomass gasifier and the hydrocarbon reforming reactor and are upstream of the methanol synthesis plant; and
where the combined syngas mixture from the biomass gasifier and the hydrocarbon reforming reactor are fed to the methanol synthesis plant, such that a majority of the carbon dioxide (CO2) produced by the biomass gasification reaction and the hydrogen (H2) produced by the hydrocarbon reforming reactor are synthesized into methanol.

2. The integrated plant of claim 1, wherein the one or more detectors are configured to perform chromatography so as to measure the sulfur content of the woody biomass and ensure that the minimized sulfur content of the woody biomass is less than the 0.05% by dry weight of the woody biomass, where the woody biomass in moist fine particle form is characterized by a decreased particle size and an overall increase in surface area due to being processed in a steam explosion unit, which is in the biomass feed system, and where the steam explosion unit, the hydrocarbon reforming reactor, and the biomass gasifier are part of the integrated plant.

3. The integrated plant of claim 1, wherein the one or more detectors are configured to work in conjunction with a stored database which maintains a listing of all those certain varieties of trees that are suitable for creating the woody biomass, and where the stored database lists at least a sulfur content and geographical location for each variety of tree, such that the woody biomass produced from each variety of tree possesses the minimized sulfur content of less than the 0.05% by dry weight of the woody biomass.

4. The integrated plant of claim 1, wherein the one or more detectors that ensure the minimized sulfur content of less than the 0.05% by dry weight of the woody biomass further ensure that the woody biomass to be fed to the biomass gasifier possesses a minimized sulfur content of less than 0.01% by dry weight of the woody biomass.

5. The integrated plant of claim 1, where the radiant high heat-flux reactor comprising the biomass gasifier is configured to react the woody biomass received from the biomass feed system in an oxidation free environment to produce the at least syngas components, including hydrogen (H2), carbon dioxide (CO2), and carbon monoxide (CO), where the carbon dioxide (CO2) comprises less than 50% by volume of the hydrogen-rich syngas including at least H2, CO2, and CO.

6. The integrated plant of claim 1, where the hydrocarbon reforming reactor is configured to supply a volume of hydrogen (H2) to the combined syngas mixture such that a ratio of the hydrogen to the sum of the carbon monoxide and the carbon dioxide (H2:(CO+CO2)) of the combined syngas mixture is between 2.1 and 2.8.

7. The integrated plant of claim 1, where the hydrocarbon reforming reactor is configured to supply a volume of hydrogen (H2) to the combined syngas mixture such that a majority of the carbon dioxide (CO2) entering the methanol synthesis plant is utilized in the synthesis of methanol.

8. The integrated plant of claim 1, where the hydrocarbon reforming reactor is configured to supply a quantity of hydrogen (H2) to the combined syngas mixture such that an exit flue gas from the methanol synthesis plant contains less than 3% of a total quantity of carbon-based molecules fed into the biomass gasifier.

9. The integrated plant of claim 1, where the hydrocarbon reforming reactor is configured to supply the quantity of hydrogen (H2) to the combined syngas mixture such that most of a total quantity of carbon-based molecules fed into the biomass gasifier are converted into methanol and subsequently gasoline, and where less than 9% of the total quantity of carbon-based molecules fed into the biomass gasifier are not converted into gasoline.

10. The integrated plant of claim 1, where the sulfur removal unit comprises of one or more sulfur guard fixed beds, an amine unit, or a combination thereof and configured to remove sulfur and other gas contaminants from the combined syngas mixture.

11. The integrated plant of claim 1, wherein the biomass feed system comprises a steam explosion unit comprising an input cavity to receive the woody biomass as a feedstock, one or more steam supply inputs, and two or more stages to pre-treat the woody biomass for subsequent supply to the biomass gasifier, where the two or more stages use a combination of heat, pressure, and moisture that are applied to the woody biomass to make the woody biomass into the moist fine particle form, where a steam explosion process breaks down a bulk structure of the received woody biomass, at least in part, by applying low-pressure steam through a first steam supply input to begin degrading bonds between lignin and hemi-cellulose from cellulose fibers of the woody biomass and increase a moisture content of the received woody biomass, then by applying high-pressure steam by way of a second steam supply input at a pressure of at least ten times atmospheric pressure to heat and pressurize any gases and fluids present within the woody biomass, and then by rapidly depressurizing the woody biomass with the increased moisture content and degraded bonds so as to internally blow apart the bulk structure of the woody biomass, thereby placing the woody biomass into the moist fine particle form, and where the woody biomass in the moist fine particle form is subsequently fed to a feed section of the biomass gasifier.

12. The integrated plant of claim 1, where the hydrocarbon reforming reactor is a Steam Methane Reformer (SMR), where the radiant high heat-flux reactor has the biomass feed system, a first steam supply inlet, a first set of sensors to measure a chemical composition of produced product gases from the radiant high heat-flux reactor, and a gasifier reactor control system to cause the biomass gasification reaction of the woody biomass in moist fine particle form at a temperature of at least 950 degrees C., the SMR reactor has a methane-based gas feed system, a second steam supply inlet, a second set of sensors to measure a chemical composition of produced product gases from the SMR reactor, and an SMR control system, and both the SMR control system and the gasifier reactor control system are part of one or more control systems, and wherein the gasifier reactor control system and the SMR control system interact to control an amount of hydrogen (H2) and carbon monoxide and carbon dioxide (CO+CO2) gases supplied to the combined syngas mixture to achieve a proper ratio of hydrogen (H2) to carbon monoxide and carbon dioxide (CO+CO2) that is higher than a ratio generally needed for methanol synthesis from 1) a first stream of the 1) hydrogen gas, 2) hydrogen-rich syngas composition, and 3) any combination of the two components from the SMR reactor, 2) a separate, second stream of the carbon dioxide (CO2) rich syngas composition from the radiant high heat-flux reactor and 3) a flow of hydrogen gas from a separator off a purge gas line coming out of the methanol synthesis plant, and any of these three sources are mixed together prior to feeding the combined syngas mixture at the proper ratio into the methanol synthesis plant.

13. The integrated plant of claim 1, where the radiant high heat-flux reactor is configured to react the woody biomass in the moist fine particle form in the rapid biomass gasification reaction at a temperature of at least 950 degrees C. primarily by way of a radiant heat emitted from the radiant high heat-flux reactor to produce reactant products including ash and syngas components of hydrogen and carbon monoxide exiting the radiant high heat-flux reactor.

14. A method in an integrated plant of improving carbon utilization of carbon molecules from gasified woody biomass to be converted into methanol, comprising:
using one or more detectors to measure a sulfur content of woody biomass, where the one or more detectors are configured to ensure a minimized sulfur content of the woody biomass of less than 0.05% by weight, such the integrated plant operates without a water-gas-shift unit and without an acid gas removal unit, where the one or more detectors are geographically located on the same site as the integrated plant;
feeding the woody biomass with the minimized sulfur content as a feedstock into a biomass feed system that includes a steam explosion unit configured to apply a combination of heat, pressure, and moisture to the woody biomass with the minimized sulfur content to make the woody biomass into a moist fine particle form;
receiving the woody biomass in the moist fine particle form from the biomass feed system into a biomass gasifier comprising a radiant high heat-flux reactor configured to react the woody biomass in moist fine particle form at a temperature of at least 950 degrees C., where the biomass gasifier has a steam supply input and one or more heat sources, and in the presence of steam the woody biomass in the moist fine particle form is reacted in the radiant high heat-flux reactor in a rapid biomass gasification reaction to produce at least syngas components, including hydrogen (H2); carbon dioxide (CO2), and carbon monoxide (CO), where the steam explosion unit and the biomass gasifier are part of the integrated plant;
receiving a methane-based gas into a hydrocarbon reforming reactor which is in parallel to and cooperates with the radiant high heat-flux reactor to produce a high-quality combined syngas mixture for methanol synthesis between the resultant reactant products coming from the two reactors, wherein the hydrocarbon reforming reactor provides 1) hydrogen gas, 2) a hydrogen-rich syngas composition, in which a ratio of hydrogen (H2) to carbon monoxide (CO) is higher than a ratio generally needed for methanol synthesis, and 3) any combination of the two, to be mixed with a potentially carbon dioxide (CO2) rich syngas composition produced by the biomass gasifier, in which a ratio of hydrogen to carbon dioxide (H2:CO2) is higher than the ratio generally needed for methanol synthesis in order to convert greater than 60% of the carbon-based molecules in the woody biomass received from the biomass feed system into methanol by way of a methanol synthesis plant;
removing at least sulfur-based contaminants from the combined syngas mixture by passing the combined syngas mixture through one or more sulfur guard fixed beds of a sulfur removal unit that are downstream of the biomass gasifier and the hydrocarbon reforming reactor and are upstream of the methanol synthesis plant, where the sulfur removal unit is configured to remove gas contaminants from the combined syngas mixture; and
feeding the combined syngas mixture to the methanol synthesis plant, such that a majority of the carbon dioxide (CO2) produced by the radiant high heat-flux reactor and the hydrogen (H2) produced by the hydrocarbon reforming reactor are synthesized into methanol.

15. The method of claim 14, wherein feeding the woody biomass with the minimized sulfur content as the feedstock into the biomass feed system further comprises:
- receiving the woody biomass as the feedstock though an input cavity into the steam explosion unit comprising one or more steam supply inputs and two or more stages to pre-treat the woody biomass for subsequent supply to the biomass gasifier, where the two or more stages apply the combination of heat, pressure, and moisture to the woody biomass to configure the woody biomass into the moist fine particle form;
- breaking down a bulk structure of the woody biomass, at least in part, by applying low-pressure steam through a first steam supply input to the steam explosion unit so as to begin degrading bonds between lignin and hemi-cellulose from cellulose fibers of the woody biomass and increase a moisture content of the woody biomass;
- applying high-pressure steam by way of a second steam supply input to the steam explosion unit at a pressure of at least ten times atmospheric pressure to heat and pressurize any gases and fluids present within the woody biomass, and
- rapidly depressurizing the woody biomass with the increased moisture content and degraded bonds so as to internally blow apart the bulk structure of the woody biomass, thereby placing the woody biomass into the moist fine particle form, where the woody biomass in the moist fine particle form is subsequently fed to a feed section of the biomass gasifier.

* * * * *